(12) United States Patent
Edwards et al.

US008093019B2

(10) Patent No.: US 8,093,019 B2
(45) Date of Patent: Jan. 10, 2012

(54) METHOD FOR CELLULASE PRODUCTION

(75) Inventors: Jason B. Edwards, Ontario (CA); Brian E. Foody, Ontario (CA); Glenn D. Munkvold, Fairfield, ME (US)

(73) Assignee: Iogen Energy Corporation, Ontario (CA)

( * ) Notice: Subject to any disclaimer, the term of this patent is extended or adjusted under 35 U.S.C. 154(b) by 433 days.

(21) Appl. No.: 12/200,492

(22) Filed: Aug. 28, 2008

(65) Prior Publication Data

US 2009/0061486 A1 Mar. 5, 2009

Related U.S. Application Data

(60) Provisional application No. 60/969,025, filed on Aug. 30, 2007.

(51) Int. Cl.
*C12P 21/04* (2006.01)
(52) U.S. Cl. .................. 435/71.1; 435/209; 435/171
(58) Field of Classification Search .................. 435/171, 435/209, 71.1
See application file for complete search history.

(56) References Cited

U.S. PATENT DOCUMENTS

| | | | |
|---|---|---|---|
| 4,461,648 A | 7/1984 | Foody | |
| 4,600,590 A | 7/1986 | Dale | |
| 5,837,515 A * | 11/1998 | Suominen et al. | 435/200 |
| 5,916,780 A | 6/1999 | Foody et al. | |
| 6,043,392 A | 3/2000 | Holtzapple et al. | |
| 6,090,595 A | 7/2000 | Foody et al. | |
| 2004/0247627 A1 * | 12/2004 | Nguyen-Xuan | 424/400 |
| 2006/0008885 A1 * | 1/2006 | Wahnon et al. | 435/105 |

FOREIGN PATENT DOCUMENTS

EP 0 133 035 A2 2/1985

OTHER PUBLICATIONS

Ju et al. Biotechnol. Progress (1999) 15: 91-97.*
Foreman et al. J. Biol. Chem. (2003) 278(34): 31988-31997.*
Kadam et al. Biotecnol. Lett. (1995) 17(10): 1111-1114.*
Nanda et al. J. General Microbiol. (1986) 132: 3201-3207.*
Kawamori et al. Appl. Microbiol. Biotechnol. (1985) 22: 235-236.*
Ahmed et al., "Inducton of Xylanase and Cellulase Genes from *Trichoderma harzianum* with Different Carbon Sources", Pakistan Journal of Biological Sciences, vol. 6, No. 22 (2003) 1912-16.
Aro et al. "ACEI of *Trichoderma reesei* is a Repressor of Cellulase and Xylanase Expression", Applied and Environmental Microbiology, vol. 69, No. 1 (2003) 56-65.
Bailey et al., "Effect of pH on production of xylanase by *Trichoderma reesei* on xylan- and cellulose-based media", Appl, Microbiol. Biotechnol., vol. 40 (1993) 224-29.
Karaffa et al., "D-Galactose induces cellulase gene expression in *Hypocrea jecorina* at low growth rates", Microbiology, vol. 152 (2006) 1507-14.
Kubicek et al., "Triggering of Cellulase Biosynthesis by Cellulose in *Trichoderma reesei*", The Journal of Biological Chemistry, vol. 268, No. 26 (1993) 19364-68.
Ilmen et al., "Regulation of Cellulase Gene Expression in the Filamentous Fungus *Trichoderma reesei*", Applied and Environmental Microbiology, vol. 63, No. 4 (1997) 1298-1306.
Lo et al., "Cellulase Production by *Trichoderma reesei* Using Sawdust Hydrolysate", Applied Biochemistry and Biotechnology, vol. 121-124 (2005) 561-73.
MacCabe et al., "Opposite Patterns of Expression of Two *Aspergillus nidulans* Xylanase Genes with Respect to Ambient pH", Journal of Bacteriology, vol. 180, No. 5 (1998) 1331-33.
Mach et al., "Regulation of Gene Expression in Industrial Fungi: *Trichoderma*", Appl. Microbiol Biotechnol, vol. 60, No. 5 (2003) 515-22.
Margeot et al., "Characterization of different enzyme cocktails secreted by *Trichoderma reesei* using 2D-electrophoresis", 29th Symposium on Biotechnology for Fuels and Chemicals (2007).
Margolles-Clark et al., "Expression patterns of ten *hemicellulase* genes of the filamentous fungus *Trichoderma reesei* on various carbon sources", Journal of Biotechnology, vol. 57 (1997) 167-79.
Miettinen-Oinonen et al., "Enhanced Production of *Trichoderma reesei* Endoglucanases and Use of the New Cellulase Preparations in Producing the Stonewashed Effect on Denim Fabric", Applied and Environmental Microbiology, vol. 68, No. 8 (2002) 3956-64.
Nakari-Setala et al., "Production of *Trichoderma reesei* Cellulases on Glucose-Containing Media", Applied and Environmental Microbiology, vol. 61, No. 10 (1995) 3650-55.
Ohgren et al., "Optimization of Steam Pretreatment of SO2-Impregnated Corn Stover for Fuel Ethanol Production", Applied Biochemistry and Biotechnology, vol. 121-124 (2005) 1055-67.
Sternberg et al., "Induction of Cellulolytic Enzymes in *Tricoderma reesei* by Sophorose", Journal of Bacteriology, vol. 139, No. 3 (1979) 761-69.
Strauss et al., "Cre1, the carbon catabolite repressor protein from *Trichoderma reesei*", FEBS Letters, vol. 376 (1995) 103-7.
Stricker et al., "Xyr1 (Xylanase Regulator 1) Regulates both the Hydrolytic Enzyme System and D-xylose Metabolism in *Hypocrea jecorina*", Eukaryotic Cell, vol. 5, No. 12 (2006) 2128-37.
Weil et al., "Pretreatment of Yellow Poplar Sawdust by Pressure Cooking in Water", Applied Biochemistry and Biotechnology, vol. 68 (1997) 21-40.
Xiong et al., "Improved xylanase production by *Trichoderma reesei* grown on L-arabinose and lactose or D-glucose mixtures" Appl. Microbiol. Biotechnol., vol. 64 (2004) 353-58.
Zeilinger et al., "Different Inducibility of Expression of the Two Xylanase Genes xyn1 and xyn2 in *Trichoderma reesei*" The Journal of Biological Chemistry, vol. 271, No. 41 (1996) 25624-629.
Fenner, et al., "Quantification of Commassie Blue Stained Proteins in Polyacrylamide Gels Based on Analyses of Elluted Dye", Anal. Biochem., vol. 63 (1975) 595-602.

(Continued)

*Primary Examiner* — Susan Hanley

(74) *Attorney, Agent, or Firm* — Fitzpatrick, Cella, Harper & Scinto

(57) ABSTRACT

A fermentation process using hemicellulose-derived carbohydrates for the production of cellulase mixtures with a high proportion of cellulases relative to hemicellulases is provided. The cellulases produced by the process of the invention are further characterized by high specific productivity. The resulting cellulase mixtures comprise at least two times more cellulase than hemicellulase and are useful for the hydrolysis of cellulosic substrated, particularly, pretreated lignocellulosic substrate.

18 Claims, 5 Drawing Sheets

OTHER PUBLICATIONS

Esterbauer, et al., "Production of Trichoderma Cellulase in Laboratory and Pilot Scale", Bioresource Technology, vol. 36, No. 1 (1991) 51-66.

Juhász, "Enzymes for improved hydrolysis of lignocellulosics", Department of Agricultural Chemical Technology Budapest University of Technology and Economics (2005) 1-61.

Mohagheghi, et al., "Production of Cellulase on Mixtures of Xylose and Cellulose in a Fed-Batch Process", Biotechnology and Bioengineering, vol. 35, No. 2 (1990) 211-16.

Muthuvelayudham, et al., "Fermentative production and kinetics of cellulase protein on *Trichoderma reesei* using sugarcane bagasse and rice straw", African Journal of Biotechnology, vol. 5, No. 20 (2006) 1873-81.

Schaffner, et al., "Cellulase Production by *Trichoderma reesei* when Cultured on Xylose-Based Media Supplemented with Sorbose", Biotechnology and Bioengineering, vol. 37, No. 1 (1991) 12-16.

Schaffner, et al., "Cellulase Production in Continuous Culture by *Trichoderma-reesei* on Xylose-Based Media", Biotechnology and Bioengineering, vol. 39, No. 8 (1992) 865-69.

\* cited by examiner (A)

(B)

(A)

(B)

(A)

(B)

(A)

(B)

METHOD FOR CELLULASE PRODUCTION

RELATED APPLICATIONS

This application claims the priority benefit of a provisional application entitled METHOD FOR FUNGAL CELLULASE PRODUCTION, Application No. 60/969,025, filed Aug. 30, 2007, the entire contents of which are incorporated herein by reference.

FIELD OF THE INVENTION

The present invention relates to a fermentation process for producing cellulases from a fungal host cell.

BACKGROUND OF THE INVENTION

Cellulose and hemicellulose constitute an important renewable and inexpensive carbon source for the production of fermentable sugars. Cellulose, consists of D-glucose units linked together in linear chains via $\beta$-1,4 glycosidic bonds. Hemicellulose consists primarily of a linear xylan backbone comprising D-xylose units linked together in via $\beta$-1,4 glycosidic bonds and numerous side chains linked to the xylose units via $\beta$-1,2 or $\beta$-1,3 glycosidic or ester bonds (e.g., L-arabinose, acetic acid, ferulic acid, etc).

*Trichoderma reesei* (the asexual anamorph of *Hypocrea jecorina*) is a filamentous fungus capable of producing a cellulase mixture comprising variety of cellulases and hemicellulases. These include two cellobiohydrolases, eight endoglucanases, four xylanases, two $\alpha$-L-arabinofuranosidases, and a beta-mannanase. *T. reesei* also produces a number of accessory enzymes that assist in the generation of monosaccharides from the cellulose and hemicellulose, including acetyl xylan esterase, beta-xylosidase and several beta-glucosidases.

The regulation of the production of cellulases and hemicellulases by *T. reesei* is complex and controlled primarily at the transcriptional level in response to available carbon sources. Glucose represses cellulase gene expression through the action of transcriptional regulators such as cre1 (Strauss, J., et al., 1995, FEBS Letters 376: 103-107) and ace1 (Aro, N., et al., 2003, Appl. Environ. Microbiol. 69: 56-65). Under glucose-limiting conditions, cellulase transcription is derepressed, with full activation of transcription requiring the presence of an inducing carbohydrate, such as cellulose, or $\beta$-linked disaccharides such as cellobiose, sophorose, gentiobiose and lactose (Ilmen, M., et al., 1997, Appl. Environ. Microbiol. 63: 1298-1306). Cellulase-inducing carbohydrates (CIC) also lead to the activation of hemicellulase transcription (Mach, R. L. and Zeilinger, S., 2003, Appl. Microbiol. Biotechnol. 60: 515-522; Margolles-Clark et al., 1997, J. Biotechnol 57: 167-179). The xyr1 gene product has been shown to participate in the transcriptional activation of both hemicellulase and cellulase genes by xylose (Stricker, A. R., et al., 2006, Eukaryotic Cell 5: 2128-2137).

Although *T. reesei* produces low levels of xylanase activity under cellulase-inducing conditions, the enzyme system produced by cultures of *T. reesei* growing on xylose or other hemicellulose-derived carbohydrates is enriched in hemicellulase activities relative to cellulase activities. Production of secreted xylanase is enhanced by xylan (Bailey, M. J., et al., 1993, Appl. Microbiol. Biotechnol. 40: 224-229) and arabinose (Xiong et al., 2004, Appl. Microbiol. Biotech 64: 353-358). Transcription of hemicellulase genes is activated further by hemicellulose or its breakdown products as well as by cellulose. In *Trichoderma reesei*, transcription of the genes encoding xylanase 1 and 2 (xln1 and xln2) is activated by cellulose, sophorose, xylan and arabinitol, and transcription of arabinofuranosidase gene abf1 is activated by arabinose, arabinitol and xylan (Margolles-Clark, et al., 1997, J. Biotechnol. 57: 167-179). However, as a result of increased xylanase expression, the relative proportion of cellulase in the secreted enzyme composition is reduced. This results in decreased specific activity of the cellulase and, as a consequence, higher dosages of total protein are needed for effective hydrolysis of cellulosic substrates.

Provision of equimolar amounts of cellobiose and xylobiose results in similar levels of xylanase activity in shake-flask batch cultures of *T. reesei* strain QM9414 (Zeilinger, S., et al., 1996, J. Biol. Chem. 271: 25624-25629). The cellulase activities produced by the two cultures were not reported. The relative proportion of xylanase secreted by *T. reesei* strain RutC30 in fed-batch culture was increased from 0.8% to 3.5% by changing the carbon source from 100% lactose to 75% lactose/25% xylose (Margeot, A., et al., poster presentation at $29^{th}$ Symposium on Biotechnology for Fuels and Chemical, Denver, Colo., USA). At the same time, the combined proportion of the four major cellulase components (cellobiohydrolases 1 and 2, endoglucanases 1 and 2) was reduced from 82% to 62%. The proportion of other hemicellulases and cellulases was not reported. Shake-flask batch cultures of *T. reesei* strain RutC30, using saw-dust hydroysates, were reported to produce similar levels of secreted cellulase activity (in terms of filter paper units per ml of culture) as cellulose hydrolysates (Lo, C -H. et al., 2005, Appl. Biochem. Biotechnol. Spring (121-124): 561-573). The saw-dust hydrolysates were produced by treatment with concentrated sulfuric acid and, in the case of saw dust, consisted of 25-40% hemicellulose-derived carbohydrates, 5-9% cellulase-inducing carbohydrates, 13-45% glucose and 2-45% oligosaccharides. However, as no information is given concerning the effect of the sawdust hydrolysates on hemicellulase activity or total secreted protein, the impact of the sawdust hydrolysates on the relative proportions of cellulose and hemicellulase in the secreted protein could not be estimated.

The relative proportion of hemicellulases can also be manipulated by adjusting the pH of the fermentation culture medium (Bailey, M. J., et al., 1993, Appl. Microbiol. Biotechnol. 40: 224-229); the proportion of xylanase activity relative to cellulase activity is enhanced at pH 6-7. The transcription of xylanase genes in *Aspergillus* are subject to regulation by pH-dependent transcriptional regulator pacC (Maccabe, A. P., et al., 1998, J. Bacteriol. 180:1331-1333).

There are situations in which it is desirable to produce cellulase mixtures with a high proportion of cellulases from fungal cultures using carbohydrate sources comprising mainly xylose and other pentose sugars derived from hemicellulose, such as those produced by chemical treatments of lignocellulosic biomass. Methods for the pretreatment of hemicellulose-containing lignocellulosic biomass are described in U.S. Pat. Nos. 4,461,648, 5,916,780, 6,090,595, 6,043,392, 4,600,590; Weil et al., 1997, *Appl. Biochem. Biotechnol.* 681: 21-40; and Öhgren, K., et al., 2005, Appl. Biochem. Biotechnol. Spring (121-124): 1055-1067 (which are incorporated herein by reference).

SUMMARY OF THE INVENTION

The present invention relates to a fermentation process for producing cellulases from a fungal host cell.

It is the object of the present invention to provide an improved method for cellulose production.

The present invention provides a fermentation process for the production of cellulase mixtures with a high proportion of cellulase relative to hemicellulase, comprising cultivating a host cell capable of producing cellulases under conditions conducive for the production of hemicellulases.

The process of producing cellulose incorporates the use of a fungal enzyme mixture from a species of *Trichoderma* or *Hypocrea* with a high cellulase:hemicellulase ratio in submerged liquid fermentations at high productivity, in which more than 40% the carbon source for said process is from hemicellulose-derived carbohydrates and more than 3% but less than 20% of the carbon source is from cellulase-inducing carbohydrates.

The present invention provides a fermentation process for the production of a cellulase mixture comprising providing a cellulase-secreting host cell of the genus *Trichoderma* or *Hypocrea* with a carbon source for cellulase enzyme production, the carbon source comprising between about 40 weight percent and about 97 weight percent of the total carbon present in the carbon source is a hemicellulose-derived carbohydrate, and between about 3 weight percent and about 20 weight percent of the total carbon present in the carbon source is a cellulase-inducing carbohydrate, for about 3 to about 30 days, at a temperature of about 20° C. to about 35° C., at a pH of from about 3.0 to about 6.5, and obtaining the cellulose mixture.

The present invention includes the fermentation process described above, wherein between about 80 weight percent and about 97 weight percent of the total carbon present in the carbon source is the hemicellulose-derived carbohydrate, and wherein between about 8 weight percent and about 15 weight percent of the total carbon present in the carbon source is the cellulase-inducing carbohydrate. Furthermore, the cellulase mixture comprises cellulases and hemicellulases in a ratio of at least 2:1, or of at least 3:1. The carbon source used in the fermentation process as described above may further comprise one or more additional carbon sources. The one or more additional carbon source may be glycerol or an organic acid. Furthermore, the fermentation process may be batch, fed-batch or continuous.

The present invention provides the fermentation process as defined above, wherein the host cell is a strain of *Trichoderma reesei*.

The present invention also provides the fermentation process as described above, wherein the process produces at least 2-fold more secreted cellulase when compared to the amount of secreted cellulase produced in a process in which the carbon source consists of hemicellulose-derived carbohydrates. The process may also be characterized by having at least a 3-fold increase in specific productivity ($q_p$) when compared to the $q_p$ of a process in which the carbon source consists of hemicellulose-derived carbohydrates. Furthermore, the process may be characterized by having at least a 5-fold increase in specific productivity ($q_p$) when compared to the $q_p$ of a process in which the carbon source consists of hemicellulose-derived carbohydrates.

The present invention is also directed to a use of the cellulase mixture produced by the fermentation process as described above for the hydrolysis of a cellulosic substrate. The cellulosic substrate may be a pretreated lignocellulosic substrate.

The present invention also provides a method of hydrolyzing a cellulosic substrate comprising,
adding the cellulase mixture produced by the fermentation process of claim 1 to a cellulosic substrate to produce a reaction mixture, wherein the concentration of the cellulosic substrate is from about 1 g/L to about 200 g/L and the cellulase mixture is added at concentration from about 0.1 to about 100 mg of protein per gm of cellulose;
incubating the reaction mixture for a period of time from about 4 hours to about 120 hours, at a temperature from about 30° C. to about 60° C., and at a pH from about 3.5 to about 7.0 to hydrolyze the cellulose and produce reaction products.

The present invention is in part based on the surprising discovery that carbohydrate sources containing hemicellulose-derived carbohydrates (HDC) and cellulase-inducing carbohydrates (CIC) can be used in a fermentation process to produce fungal cellulase mixtures with a high proportion of cellulase and a correspondingly low proportion of hemicellulase. The productivity of the fermentation process is significantly higher than the same process using only hemicellulase-derived carbohydrate.

BRIEF DESCRIPTION OF THE DRAWINGS

These and other features of the invention will become more apparent from the following description in which reference is made to the appended drawings wherein.

DESCRIPTION OF PREFERRED EMBODIMENT

Figure 1:
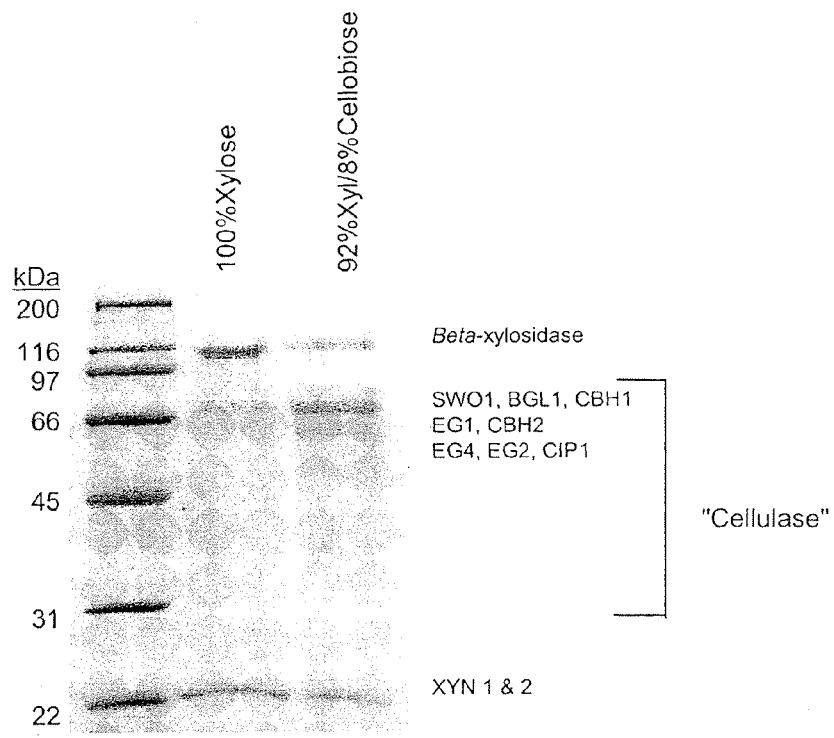
FIG. 1 shows SDS polyacrylamide gel electrophoresis (SDS-PAGE) analysis of the cellulase mixtures produced and secreted by *T. reesei* strains RutC30 (A) and P59G (B) in 14 L fed-batch fermentations in which the carbohydrate fed to the fermentation consisted of 0-15% cellulase-inducing carbohydrate (cellobiose for RutC30 or a CIC cocktail for P59G) and 85-100% xylose.
Figure 1:
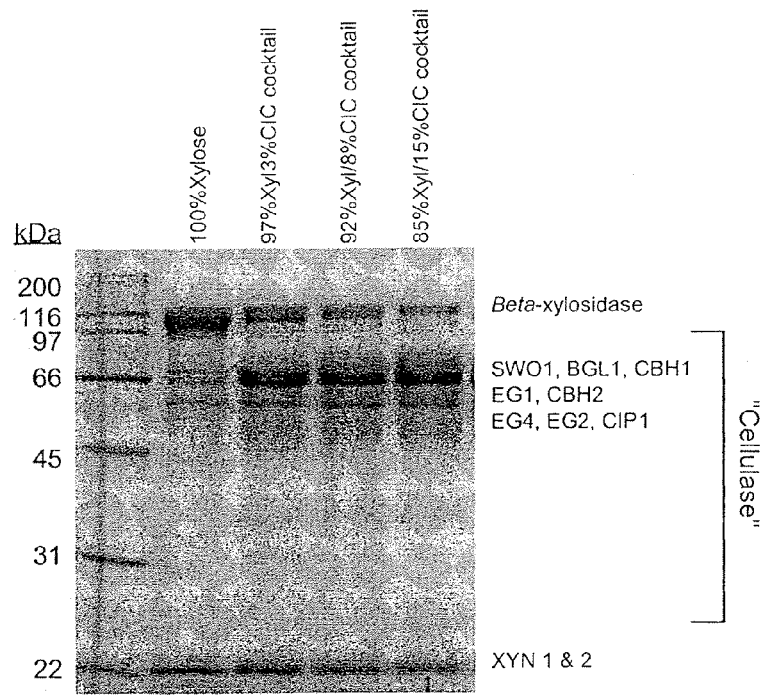
Figure 2:
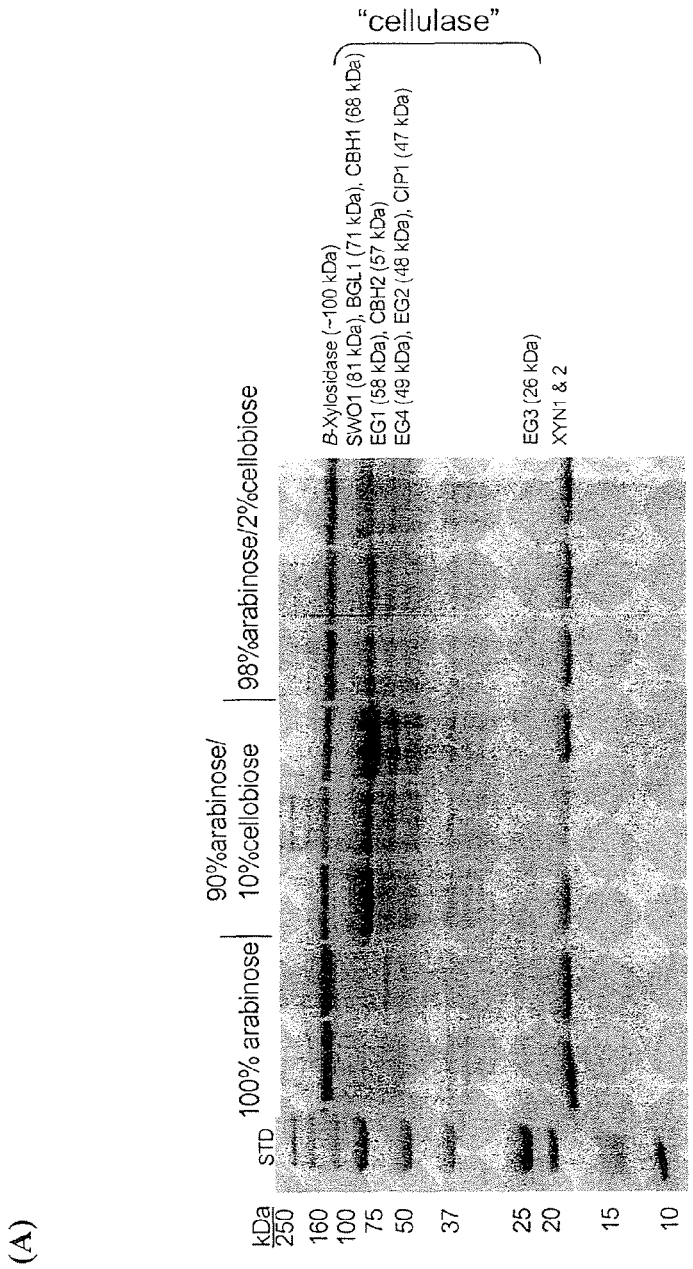
FIG. 2 shows SDS polyacrylamide gel electrophoresis (SDS-PAGE) analysis of the cellulase mixtures produced and secreted by *T. reesei* strain P59G in 14 L fed-batch fermentations in which the carbohydrate fed to the fermentation consisted of 0%, 2% or 10% cellulase-inducing carbohydrate and 100%, 98% or 90% arabinose.

The present invention relates to a fermentation process for producing cellulases from a fungal host cell.

The following description is of a preferred embodiment by way of example only and without limitation to the combination of features necessary for carrying the invention into effect.

The present invention provides a production of cellulase from fermentation of fungal cells, preferably in submerged liquid culture fermentations.

Process of Producing Cellulase Mixtures

Cellulase mixtures may be produced by subjecting an actively growing fungal culture to media (solid or liquid) containing little or no glucose and a cellulase-inducing carbohydrate (CIC), as well as other nutrients required for cell growth, at temperatures and pH suitable for the host cell. As described herein, any known process for producing cellulose may be used wherein the inducer, such as pure cellulose, is replaced by a carbohydrate source comprising hemicellulose derived carbohydrates (HDC) and cellulase-inducing carbohydrates (CIC), preferably from about 40% to about 97% HDC, or any amount therebetween, and from about 3% to about 20% CIC, or any amount therebetween. For example, from about 40, 42, 44, 46, 48, 50, 52, 54, 56, 58, 60, 62, 64, 66, 68, 70, 72, 74, 76, 78, 80, 82, 84, 86, 88, 90, 92, 94, 96, 97% HDC, or any amount therebetween, and from about 3, 4, 6, 7, 8, 9, 10, 12, 14, 16, 18, 20% CIC, or any amount therebetween.

Submerged liquid fermentations of *Trichoderma* and related filamentous fungi are typically conducted as a batch, fed-batch or continuous process. In a batch process, all the necessary materials, with the exception of oxygen for aerobic processes, are placed in a reactor at the start of the operation and the fermentation is allowed to proceed until completion, at which point the product is harvested. In a fed-batch process, the culture is fed continuously or sequentially with one or more media components with the removal of the culture fluid. In a continuous process, fresh medium is supplied and culture fluid is removed continuously at volumetrically equal rates to maintain the culture at a steady growth rate.

The process of the present invention may be performed as a batch, fed-batch, a repeated fed-batch, a continuous process or any combination thereof. For example, the process may be a fed-batch process.

The process of the present invention may be carried at a temperature from about 20° C. to about 35° C., or any temperature therebetween, for example from about 25° C. to about 30° C., or any temperature therebetween, or from 20, 22, 25, 26, 27, 28, 29, 30, 32, 35° C., or any temperature therebetween.

The process of the present invention may be carried out at a pH from about 3.0 to 6.5, or any pH therebetween, for example from about pH 3.5 to pH 5.5, or any pH therebetween, for example from about pH 3.0, 3.2, 3.4, 3.5, 3.7, 3.8, 4.0, 4.1, 4.2, 4.3, 4.4, 4.5, 4.6, 4.7, 4.8, 4.9, 5.0, 5.2, 5.4, 5.5, 5.7, 5.8, 6.0, 6.2, 6.5 or any pH therebetween.

The process of the present invention may be carried out over a period of 3-30 days, or any amount therebetween, for example between 3 and 10 days, or any amount therebetween, between 4 and 8 days, or any amount therebetween, or from 3, 4, 5, 6, 7, 8, 9, 10, 12, 14, 16, 18, 20, 22, 24, 26, 28, 30 days, or any amount therebetween.

The process of the present invention may be performed in cultures of at least 1 liter, for example from about 1 to about 400,000 liters, or any amount therebetween, for example, 10 to about 400,000 liters, or any amount therebetween, 1,000 to about 200,000 liters, or any amount therebetween, or 10,000 to about 200,000 liters, or any amount therebetween, or from about 1, 10, 50, 100, 200, 400, 600, 800, 1000, 2000, 4000, 6000, 8000 10,000, 15,000, 20,000, 25,000, 30,000, 35,000, 40,000, 45,000, 50,000, 55,000, 60,000, 65,000, 70,000, 75,000, 80,000, 85,000, 90,000, 95,000, 100,000, 150,000, 200,000, 300,000, 400,000 liters in volume, or any amount therebetween.

The process of the present invention may be performed aerobically, in the presence of oxygen, or anaerobically, in the absence of oxygen. For example, the process may be performed aerobically.

The fermentation process of the present invention may produce at least 2.5-fold, more preferably 3-fold, more secreted protein than a corresponding process in which the carbon source contains only HDC and is performed using a fungal strain that has not been modified or selected for enhanced activation of cellulase production by HDC. For example the process described herein may produce 2.5 to about 10 fold more, or any amount therebetween, for example about 2.5, 2.6, 2.8, 3.0, 3.2, 3.4, 3.6, 3.8, 4.0, 4.2, 4.4, 4.6, 4.8, 5.0, 5.2, 5.4, 5.6, 5.8, 6.0, 6.2, 6.4, 6.6, 6.8, 7.0, 7.2, 7.4, 7.6, 7.8, 8.0, 8.2, 8.4, 8.6, 8.8, 9.0, 9.2, 9.4, 9.6, 9.8, 10 fold more secreted protein, or any amount therebetween or more than 10 fold more secreted protein, than a corresponding process in which the carbon source contains only HDC and is performed using a fungal strain that has not been modified or selected for enhanced activation of cellulase production by HDC. Thus, the fermentation process may be characterized by having at least a 3-fold, more preferably a 5-fold, or any amount therebetween, increase in specific productivity ($q_p$) in terms of mg secreted cellulase produced/ gm biomass /h than a corresponding process in which the carbon source contains only HDC and is performed using a fungal strain that has not been modified or selected for enhanced activation of cellulase production by HDC. An increase in specific productivity of protein production in the present of varying amount of HDC, CIC, or both HDC and CIC as described herein, is shown in Table 1.

TABLE 1

Production of protein and fungal cells from submerged liquid cultures of *T. reesei* strains grown on HDC plus 0-20% CIC in 14L fed-batch fermentations.

| Strain | HDC (%) | % CIC | Final Protein (g/L)[c] | Final cells (g/L)[c] | $q_p$ (mg protein/g cells/h) |
|---|---|---|---|---|---|
| P59G | Xylose (100) | 0 | 8 | 41 | 2 |
|  | Xylose (97) | 3[a] | 25 | 35 | 14 |
|  | Xylose (92) | 8[a] | 32 | 32 | 19 |
|  | Xylose (85) | 15[a] | 32 | 25 | 24 |
|  | Arabinose (100) | 0[b] | 5 | 30 | 3.5 |
|  | Arabinose (98) | 2[b] | 25 | 27 | 7 |
|  | Arabinose (90) | 10[b] | 0.66 | 13 | 14 |
| RutC30 | Xylose (100) | 0[b] | 3.6 | 6.9 | 4 |
|  | Xylose (92) | 8[b] | 8 | 41 | 23 |

[a]CIC for these fermentations was inducing cocktail comprising, as a function of total carbohydrate, 56% gentiobiose, 14% sophorose, 6% cellobiose, 10% trehalose, 6% maltotriose, 4% glucose and 14% other carbohydrates
[b]CIC for these fermentations was cellobiose.
[c]For strain P59G, reported values are the average results of three (xylose) or two (arabinose) replicate fermentations; for strain RutC30, the reported values are the results from single fermentations.

Fermentation Media

In embodiments of the present invention, the fungal cells are supplied with at least two carbon sources during the fermentation process: a hemicellulose-derived carbohydrate (HDC) and a cellulase-inducing carbohydrate (CIC).

As used herein, the term hemicellulose-derived carbohydrate or HDC refers to one or more oligo-, di- or monosaccharide that is derived from hemicellulose and can be utilized by the host microbe for growth, enzyme production or both. Non-limiting examples of HDC include xylo-oligosaccharides, arabinoxylo-oligosaccharides, D-xylose, xylobiose, L-arabinose, D-mannose and D-galactose. Preferably, the HDC contains D-xylose and/or L-arabinose. The carbon derived from the HDC represents from about 40% to about 97% of the total carbon fed to the fungal cells during the fermentation process. For example, the carbon derived from the HDC may represent 40%, 45%, 50%, 55%, 60%, 65%, 70%, 75%, 80%, 85%, 90%, 95%, 97%, or any amount therebetween, of the total carbon fed to the fungal cells during the fermentation process. For example, the carbon derived from the HDC may represent from about 80% to about 97% of the total carbon fed to the fungal cells during the fermentation process.

As used herein, the term cellulase-inducing carbohydrate or CIC refers to one or more oligo-, di- or mono-saccharide that leads to the induction of cellulase production by the host cell. Preferably, the CIC is one or more of cellobiose, sophorose, or gentiobiose. The CIC may be produced by enzymatic hydrolysis of cellulose with one or more cellulase enzymes to produce mainly beta-linked glucose dimers. Alternatively, a high concentration glucose syrup can be condensed to form mixtures of glucose dimers. The condensation reaction to produce glucose may be catalyzed by dilute acid and performed at temperatures above 120-150° C., or by beta-glucosidase or cellulase enzymes at more moderate temperatures of about 40-70° C. (U.S. patent application U.S.2004/0121446A1). The practice of the present invention is not limited by the method used to produce the CIC.

Preferably, the carbon derived from the CIC represents from about 3% to about 20%, or any amount therebetween, of the total carbon fed to the fungal cells during the fermentation process. For example, the carbon derived from the CIC may represent 3%, 4%, 5%, 6%, 7%, 8%, 9%, 10%, 11%, 12%, 13%, 14%, 15%, 16%, 17%, 18%, 19% or 20%, or any amount therebetween, of the total carbon fed to the fungal cells during the fermentation process. For example, the carbon derived from the CIC represents from about 8% to about 15%, or any amount therebetween, of the total carbon fed to the fungal cells during the fermentation process.

In addition to HDC and CIC, from about 0.1 to about 20%, or any amount therebetween, of the total carbon supplied to the host cell during the fermentation process may comprise one or more of glucose, glycerol, organic acids or other carbon sources that can be utilized by the host cell. For example, from about 0.1, 0.2, 0.4, 0.6, 0.8, 1.0, 1.5, 2.0, 2.5, 3.0, 3.5, 4.0, 4.5, 5.0, 6.0, 7.0, 8.0, 9.0, 10.0, 12.0, 14.0, 16.0, 18.0, 20%, or any amount therebetween, of the total carbon supplied to the host cell during the fermentation process may comprise one or more of glucose, glycerol, organic acids or other carbon sources that can be utilized by the host cell.

In the case of batch fermentation, the carbon source may be added to the fermentation medium prior to or simultaneously with inoculation. In the cases of fed-batch or continuous operations, the carbon source may also be supplied continuously or intermittently during the fermentation process. Preferably, the feed rate is between 0.2 and 2.5 g carbon/L of culture/h, or any amount therebetween. More preferably, the feed rate is between 0.4 and 1.6 g carbon/L of culture/h, or any amount therebetween.

One of skill in the art is aware that other nutrients, vitamins and minerals can be added to the fermentation media to improve growth and enzyme production of the host cell. These other media components may be added prior to, simultaneously with or after inoculation of the culture with the host cell. Organic nitrogen sources such as amino acids and peptides are sometimes used as sources of carbon; however, these organic nitrogen sources are not included in the calculation of total carbon supplied to the host cell during the fermentation process.

Following fermentation, the fermentation broth containing the cellulase enzyme may be used directly, or the cellulase enzyme may be separated from the fungal cells, for example by filtration or centrifiguation. Low molecular solutes such as unconsumed components of the fermentation medium may be removed by ultrafiltration. The cellulase enzyme maybe concentrated, for example, by evaporation, precipitation, sedimentation or filtration. Chemicals such as glycerol, sucrose, sorbitol and the like may be added to stabilize the cellulase enzyme. Other chemicals, such as sodium benzoate or potassium sorbate, may be added to the cellulase enzyme to prevent growth of microbial cont.

Fungal Cells for Cellulase Production

The fungal cell for the process may be any filamentous fungus belonging to the family *Acomycotina* or *Basidiomycotina*, such as species of *Trichoderma Hypocrea, Aspergillus, Humicola, Neurospora, Orpinomyces, Gibberella, Emericella, Chaetomium, Fusarium, Penicillium, Magnaporthe*, or *Phanerochaete*. Preferably, the host cell is a species of *Trichoderma* or *Hypocrea*. Most preferably, the host cell is a strain of *Trichoderma reesei*.

The fungal cell may be modified so as to enhance or reduce the production and secretion of one or more homologous or heterologous proteins. For example, the fungal cell may be modified with one or more genetic constructs comprising a gen encoding a cellulase enzyme operably linked to a promoter that is inducible by HDC and/or CIC. For example, the fungal cell may be modified so as to over express a beta-glucosidase enzyme according to U.S. Pat. No. 6,015,703. The host cell may also be modified so as to produce an optimized blend of cellulase components and accessory components according to co-pending U.S. Patent Applications U.S. 2008/0057541 A1 and 60/969,046. Methods to prepare genetic constructs comprising CIC or HDC inducible promoters operably linked to a cellulase gene and methods to genetically modify fungal strains include those known to those of skill in the art, including but not limited to, treatment of cells with $CaCl_2$, electroporation, biolistic bombardment, PEG-mediated fusion of protoplasts (U.S. Pat. No. 6,015,703 and U.S. Pat. No. 6,939,704).

Cellulase Mixtures

As used herein, a cellulase mixture is that mixture of cellulases, hemicellulase and other protein secreted by the fungal cell during the fermentation process. The cellulase mixture produced using the fermentation process of the present invention preferably contains a ratio of cellulase:hemicellulase components from about greater than about 2:1 (Table 2). More preferably, the cellulase:hemicellulase ratio is at least about 3:1. Most preferable, the cellulase:hemicellulase ratio is at least about 4:1. For example, the hemicellulase:cellulase ratio may be about 2:1, 2.5:1, 3:1, 3.5:1, or 4:1, or any ratio therebetween.

TABLE 2

Composition of secreted enzyme from *T. reesei* cultures grown in submerged liquid cultures on HDC and CIC in 14L fed-batch fermentation.

| Strain | HDC (%) | % CIC | Cellulase:Hemicellulase ratio* |
|---|---|---|---|
| P59G** | Glucose control (85) | 15 | 20:1 |
| | Xylose (100) | 0 | ~1:1 |
| | Xylose (97) | $3^a$ | 2:1 |
| | Xylose (92) | $8^a$ | 2:1 |
| | Xylose (85) | $15^a$ | 3:1 |
| | Arabinose (100) | $0^b$ | 0.8:1 |
| | Arabinose (98) | $2^b$ | 1.5:1 |
| | Arabinose (90) | $10^b$ | 2.4:1 |

TABLE 2-continued

Composition of secreted enzyme from *T. reesei* cultures grown in submerged liquid cultures on HDC and CIC in 14L fed-batch fermentation.

| Strain | HDC (%) | % CIC | Cellulase:Hemicellulase ratio* |
|---|---|---|---|
| RutC30 | Xylose (100) | $0^b$ | 2:1 |
|  | Xylose (92) | $8^b$ | 3:1 |

*Determined by scanning densitometry of SDS-PAGE analysis of the proteins secreted into the fermentation broth under each condition as described in Example 4.
**Relative hydrolysis activity on a pretreated lignocellulosic substrate as described in Example 4.
$^a$CIC for these fermentations was inducing cocktail comprising, as a function of total carbohydrate, 56% gentiobiose, 14% sophorose, 6% cellobiose, 10% trehalose, 6% maltotriose, 4% glucose and 14% other carbohydrates
$^b$CIC for these fermentations was cellobiose.

Hydrolysis of Cellulosic Substrates

The secreted cellulase enzymes produced using the fermentation process of the present invention are useful for the hydrolysis of a cellulosic substrate. By the term "cellulosic substrate", it is meant any substrate derived from plant biomass and comprising cellulose, including, but not limited to, pre-treated lignocellulosic feedstocks for the production of ethanol or other high value products, animal feeds, forestry waste products, such as pulp and wood chips, and textiles. The activity of secreted cellulose enzymes on pretreated lignocellulose and filter paper is presented in Table 3.

TABLE 3

Activity of cellulase mixtures from *T. reesei* cultures grown in submerged liquid cultures on HDC and CIC in 14L fed-batch fermentation.

| Strain | HDC (%) | % CIC | Relative activity on pretreated lignocellulose** | Relative activity on filter paper** |
|---|---|---|---|---|
| P59G** | Glucose control (85) | 15 | 1.0 | n.d. |
|  | Xylose (100) | 0 | n.d. | 0.11 |
|  | Xylose (92) | $8^a$ | 0.58 | 0.41 |
|  | Xylose (85) | $15^a$ | 0.62 | n.d. |
|  | Arabinose (100) | $0^b$ | n.d. | 0.05 |
|  | Arabinose (98) | $2^b$ | 0.31 | n.d. |
|  | Arabinose (90) | $10^b$ | 0.84 | 0.66 |
| RutC30 | Xylose (100) | $0^b$ | n.d. | <0.05 |
|  | Xylose (92) | $8^b$ | n.d | 0.38 |

*Determined by scanning densitometry of SDS-PAGE analysis of the proteins secreted into the fermentation broth under each condition as described in Example 4.
**Relative hydrolysis activity on a pretreated lignocellulosic substrate as described in Example 4; n.d. = not determined
$^a$CIC for these fermentations was inducing cocktail comprising, as a function of total carbohydrate, 56% gentiobiose, 14% sophorose, 6% cellobiose, 10% trehalose, 6% maltotriose, 4% glucose and 14% other carbohydrates
$^b$CIC for these fermentations was cellobiose.

The cellulase enzyme produced by the fermentation process of the present invention may be used for the enzymatic hydrolysis of a "pretreated lignocellulosic feedstock". A pretreated lignocellulosic feedstock is a material of plant origin that, prior to pretreatment, contains at least 20% cellulose (dry wt), more preferably greater than about 30% cellulose, even more preferably greater than 40% cellulose, and at least 10% lignin (dry wt), more typically at least 12% (dry wt) and that has been subjected to physical and/or chemical processes to make the fiber more accessible and/or receptive to the actions of cellulolytic enzymes. Non-limiting examples of pretreatment processes include chemical treatment of a lignocellulosic feedstock with sulfuric or sulfurous acid, or other acids; ammonia, lime, ammonium hydroxide, or other alkali; ethanol, butanol, or other organic solvents; or pressurized water (See U.S. Pat. Nos. 4,461,648, 5,916,780, 6,090,595, 6,043,392, 4,600,590, Weil et al., 1997, Appl. Biochem. Biotechnol. 681: 21-40, and Öhgren, K., et al., 2005, Appl. Biochem. Biotechnol. Spring (121-124): 1055-1067; which are incorporated herein by reference).

For example, the cellulosic substrate, may be incubated with the cellulase enzyme produced using the methods described herein, at a concentration of from about 1 to about 200 g cellulose per L of reaction mixture, or any amount there between, for example from about 1, 5, 10, 15, 20, 25, 30, 40, 50, 60, 70, 80, 90, 100, 120, 140, 160, 180, 200, or any amount therebetween, and with a cellulase dosage of from about 0.1 to about 100 mg protein per g cellulose, or any amount therebetween, for example from about 0.1, 0.5, 1.0, 2.0, 5.0, 10, 20, 30, 40, 50, 60, 70, 80, 90, 100 mg protein/g cellulose, or any amount therebetween. The reaction mixture may be incubated for from about 4 hours to about 120 hours, or any amount therebetween, at a temperature from about 30° to about 60° C., or any temperature therebetween, for example from about 30, 35, 40, 45, 50, 55, 60° C. or any temperature therebetween, and at a pH from about 3.5 to about 7.0, or any pH therebetween, for example from of pH of about 3.5, 4.0, 4.5, 5.0, 5.5, 6.0, 6.5, 7.0 or of any pH therebetween. Following incubation, the reaction products, including hemicellulose-derived carbohydrates, cellulase-inducing carbohydrates, glucose, oligosaccharides can be used for further processing, for example as a substrate for producing ethanol, butanol, sugar alcohols, lactic acid, acetic acid, or the end products may be concentrated and purified using standard methods as known in the art.

In summary, the present invention provides highly productive fermentation processes that produce cellulase enzymes with low hemicellulase content useful for the hydrolysis of cellulosic substrates.

The above description is not intended to limit the claimed invention in any manner. Furthermore, the discussed combination of features might not be absolutely necessary for the inventive solution.

EXAMPLES

The present invention will be further illustrated in the following examples. However, it is to be understood that these examples are for illustrative purposes only and should not be used to limit the scope of the present invention in any manner.

Example 1 describes the strains used in the following examples. Example 2 describes a fed-batch and continuous fermentation process using HDC and CIC. Example 3 describes the determination of specific productivity and process yields for fed-batch fermentations process using HDC and CIC. Example 4 describes the characterization of cellulase mixtures produced in fed-batch fermentations using HDC and CIC.

Example 1

*Trichoderma reesei* Strains

*T. reesei* strains RutC30 (ATCC #56765; Montenecourt, B. and Eveleigh, D. 1979. Adv. Chem. Ser. 181: 289-301) or P59G were used in the following examples. Strain P59G is a genetically modified strain that produces and secretes high levels of the beta-glucosidase encoded by *T. reesei* bgl1 as described in U.S. Pat. No. 6,015,703. The parent strain of P59G, strain BTR213, is a derivative of RutC30 produced by random mutagenesis and first selected for ability to produce larger clearing zones on minimal media agar containing 1% acid swollen cellulose and 4 g $L^{-1}$ 2-deoxyglucose and then selected for the ability to grow on lactose media containing 0.2 µg/ml carbendazim.

Example 2

Fermentations Using Mixtures of HDC and CIC

Trichoderma spores from frozen (−80° C.) 15% glycerol stocks were inoculated onto standard 85 mm petri plates containing potato dextrose agar (PDA). These plates were incubated at 28° C. for 3-5 days to achieve a confluent growth of fresh green spores. To prepare the inoculum for fermentation testing, spores from a single PDA plate were transferred to 2 L, baffled Erlenmeyer flask containing 750 mL of liquid Berkley media (pH 5.5) supplemented with 5.1 g/L of corn steep liquor powder and 10 g/L glucose. Flasks were incubated at 28° C. for 3 days using an orbital agitator (Model G-52 New Brunswick Scientific Co.) running at 100 rpm.

Berkley Media for Flasks

| Component | g/L |
|---|---|
| $(NH_4)_2SO_4$ | 1.4 |
| $KH_2PO_4$ | 2.00 |
| $MgSO_4 \cdot 7H_2O$ | 0.31 |
| $CaCl_2 \cdot 2H_2O$ | 0.53 |
| Dry Corn Steep Liquor | 5.1 |
| Glucose | 10 |
| Trace elements* | 1 mL/L |

*Trace elements solution contains 5 g/L $FeSO_4 \cdot 7H_2O$; 1.6 g/L $MnSO_4 \cdot H_2O$; 1.4 g/L $ZnSO_4 \cdot 7H_2O$.

2a. Fed-Batch Fermentations

The contents of an inoculum flask were transferred to a 14 L pilot scale fermentation vessel (Model MF114 New Brunswick Scientific Co.) set up with 10 L of Initial Pilot Media (pH 5.5). The vessel was run in batch mode until glucose in the media was depleted. At this point, the carbon source was added, on a continuous basis, from a stock that was typically 36 w % solids. Peristaltic pumps were used to deliver the carbon source at a feed at a rate of 0.4 grams of carbon/liter culture/hour. Operational parameters during both the batch and fed-batch portions of the run were: mixing by impeller agitation at 500 rpm, air sparging at 8 standard liters per minute, and a temperature of 28° C. Culture pH was maintained at 4.0-4.5 during batch growth and pH 3.5 during cellulase production using an automated controller connected to an online pH probe and a pump enabling the addition of a 10% ammonium hydroxide solution. Periodically, 100 mL samples of broth were drawn for biomass and protein analysis. The total fermentation time is typically between 96-144 hours.

Initial Media for Fed-Batch Fermentations

| Component | g/L |
|---|---|
| $(NH_4)_2SO_4$ | 2.20 |
| $KH_2PO_4$ | 1.39 |
| $MgSO_4 \cdot 7H_2O$ | 0.70 |
| $CaCl_2 \cdot 2H_2O$ | 0.185 |
| Dry Corn Steep Liquor | 6.00 |
| Glucose | 13.00 |
| Trace elements* | 0.38 mL/L |

*Trace elements solution contains 5 g/L $FeSO_4 \cdot 7H_2O$; 1.6 g/L $MnSO_4 \cdot H_2O$; 1.4 g/L $ZnSO_4 \cdot 7H_2O$.

The biomass content of fermentor broth was determined using aliquots of 5-10 mL that had been weighed, vacuum filtered through glass microfibre, and oven dried at 100° C. for 4 to 24 hours. The concentration of biomass was determined according to the equation below.

$$\text{Biomass}(g/L) = \frac{\text{dry filter paper and cake (g)} - \frac{\text{filter mass (g)}}{\text{wet sample mass (g)}}}{} \times \text{broth density (g/mL)} \times 1000 \text{ (mL/L)}$$

The protein concentration of fermentation broth filtrate was determined using the Bradford assay. Colour intensity changes in the Coomassie Brilliant Blue G-250 dye, that forms the basis of this assay, were quantified spectrophotometrically using absorbance measurements at 595 nm. The standard assay control used was a cellulase mixture of known composition and concentration.

Figure 3:
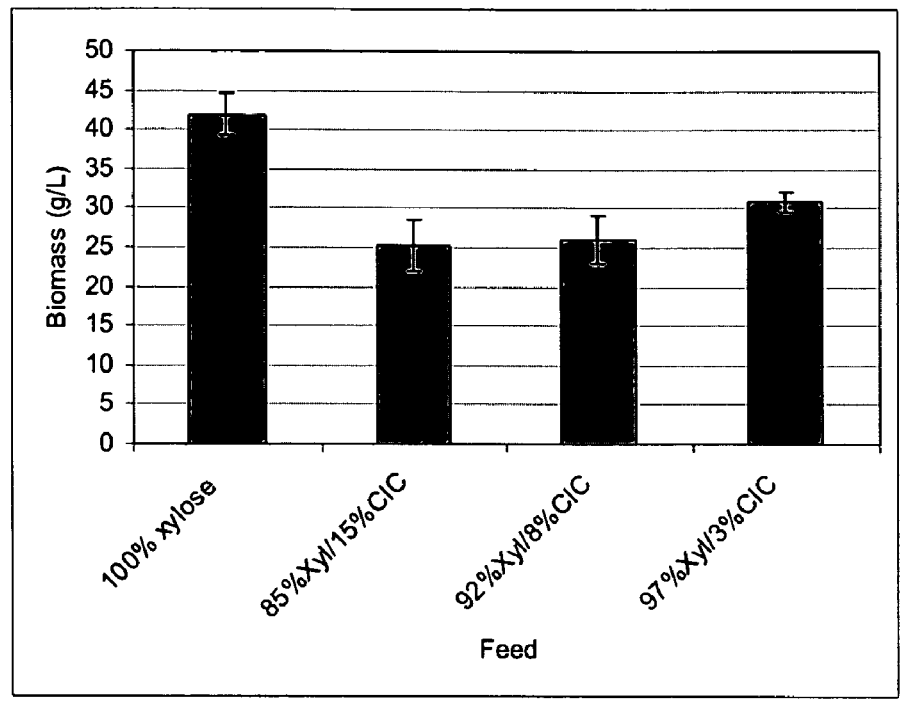
FIG. 3 shows the amount of biomass produced by *T. reesei* strain P59G in 14 L fed-batch fermentations in which the carbohydrate fed to the fermentation consisted of (A) 0-15% CIC cocktail plus 85-100% xylose as shown or (B) 0-10% cellobiose plus 90-100% arabinose. Each bar shows the average and standard deviation of three independent fermentations.
Figure 3:
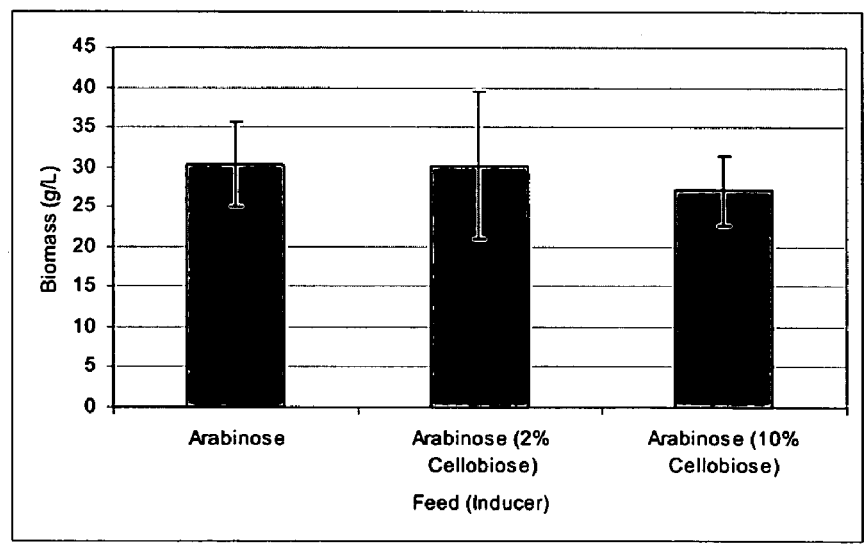

The fed-batch fermentation processes using both HDC and CIC produced 3-5 fold more protein and anywhere from 10% to 46% less biomass than corresponding processing using only HDC (Table 4, FIG. 3).

TABLE 4

Production of secreted protein and fungal cell mass in 14L fed-batch cultures of *T. reesei* strains used HDC with or without CIC.

| Strain | Carbon Source (HDC/CIC) | Average final protein (g/l)[b] | Average final cells (g/l)[b] |
|---|---|---|---|
| P59G | 100% xylose | 8 | 41 |
| | 97% xylose/3% CIC[a] | 25 | 35 |
| | 92% xylose/8% CIC[a] | 32 | 32 |
| | 85% xylose/15% CIC[a] | 32 | 25 |
| | 100% arabinose | 5 | 30 |
| | 90% arabinose/10% cellobiose | 25 | 27 |
| RutC30 | 100% xylose | 0.66 | 13 |
| | 92% xylose/8% cellobiose | 3.6 | 6.9 |

[a]CIC: inducing cocktail comprising, as a function of total carbohydrate, 56% gentiobiose, 14% sophorose, 6% cellobiose, 10% trehalose, 6% maltotriose, 4% glucose and 14% other carbohydrates.
[b]For strain P59G, reported values are the average results of three (xylose) or two (arabinose) replicate fermentations; for strain RutC30, the reported values are the results from single fermentations.

2b. Continuous Fermentations

*Trichoderma inoculum* flasks were prepared as in Example 2a, above.

The contents of an inoculum flask were transferred to a 14 L pilot scale fermentation vessel (Model MF114 New Brunswick Scientific Co.) set up with 5 L of Initial Pilot Media (pH 5.5) as described in Example 2a, above. The vessel was run in batch mode until glucose in the media was depleted. At this point, a carbon source and fresh nutrients were added, on a continuous basis.

Peristaltic pumps were used to deliver the carbon source at a feed at a rate of between 0.85 and 1.1 grams of carbon/liter culture/hour at a dilution rate of 0.025 $h^{-1}$. The carbon source consisted of 92% HDC and 8% CIC as a function of total carbohydrate. The HDC was either a mixture of pure xylose, glucose and arabinose or a pretreatment hydrolysate, produced by the pretreatment of wheat straw, and consisted of 81.1% xylose, 11.1% glucose and 7.8% arabinose. The CIC was an inducing cocktail with the composition shown below. Culture volume was maintained at 5 L during the entire fermentation through the use of a siphon. Operational parameters during both the batch and fed-batch portions of the run were: mixing by impeller agitation at 500 rpm, air sparging at 8 standard liters per minute, and a temperature of 28° C. Culture pH was maintained at 4.0-4.5 during batch growth and pH 3.5 during cellulase production using an automated controller connected to an online pH probe and a pump enabling the addition of a 10% ammonium hydroxide solution. Periodically, 100 mL samples of broth were drawn for biomass and protein analysis. The total fermentation time was typically 24 hours for the batch phase and 144 hours for the continuous phase.

| Composition of continuous fermentation nutrient media | |
|---|---|
| Component | g/kg |
| $(NH_4)_2SO_4$ | 1.68 |
| $KH_2PO_4$ | 1.06 |
| $MgSO_4 \cdot 7H_2O$ | 0.53 |
| $CaCl_2 \cdot 2H_2O$ | 0.11 |
| Dry Corn Steep Liquor | 2.52 |
| Trace elements* | 0.29 (mL/L) |
| Sugars (Xylose, Arabinose, Glucose) and [a]CIC | 97 |

*Trace elements solution contains 5 g/L $FeSO_4 \cdot 7H_2O$; 1.6 g/L $MnSO_4 \cdot H_2O$; 1.4 g/L $ZnSO_4 \cdot 7H_2O$.
[a]CIC: inducing cocktail comprising, as a function of total carbohydrate, 56% gentiobiose, 14% sophorose, 6% cellobiose, 10% trehalose, 6% maltotriose, 4% glucose and 14% other carbohydrates The content of fermentor broth and the protein concentration of the broth filtrate were determined as in Example 2a. As shown in Table 5, the cultures grown using HDC mixtures of pure sugars or pretreatment hydrolysate produce similar amounts of protein and cells.

TABLE 5

Production of secreted protein and fungal cell mass in 14L continuous cultures of *T. reesei* using CIC and HDC mixtures from pretreatment hydrolysate or pure chemicals

| Strain | Carbon Source (HDC/CIC) | Average secreted protein (g/l)[b] | Average cells (g/l)[b] |
|---|---|---|---|
| P59G | Control: 92% Pure sugars/8% [a]CIC | 14 | 15 |
|  | 92% HDC/8% CIC[a] | 14 | 20 |

[a]CIC: inducing cocktail comprising, as a function of total carbohydrate, 56% gentiobiose, 14% sophorose, 6% cellobiose, 10% trehalose, 6% maltotriose, 4% glucose and 14% other carbohydrates.
[b]Reported values are the average results of two replicate fermentations;.

Example 3

Specific Productivity

Figure 4:
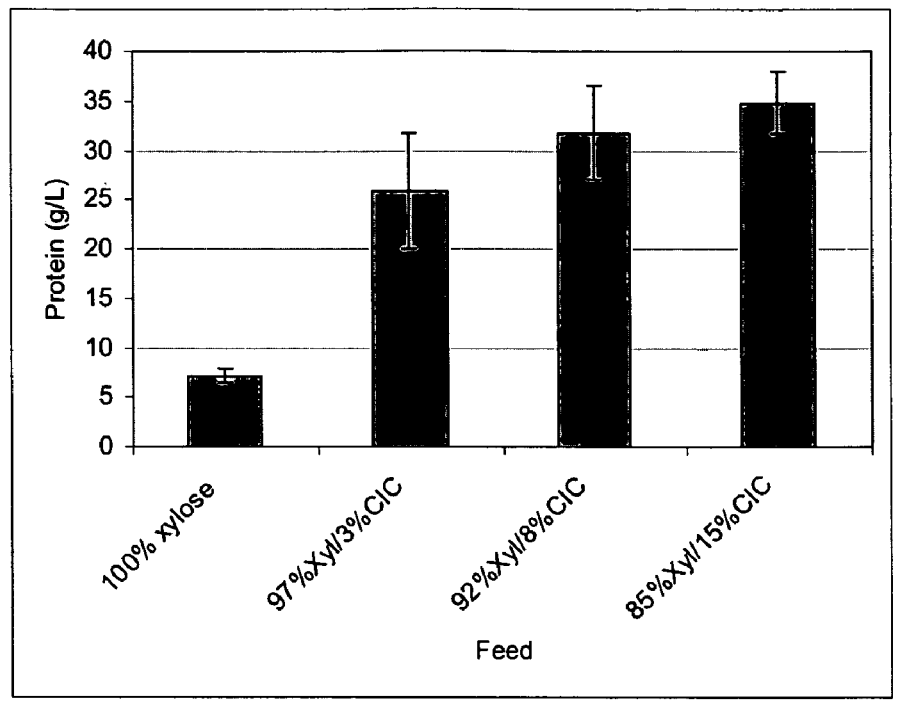
FIG. 4 shows the amount of secreted protein produced by *T. reesei* strain P59G in 14 L fed-batch fermentations in which the carbohydrate fed to the fermentation consisted of (A) 0-15% CIC cocktail plus 85-100% xylose as shown or (B) 0-10% cellobiose plus 90-100% arabinose. Each bar shows the average and standard deviation of three independent fermentations.
Figure 4:
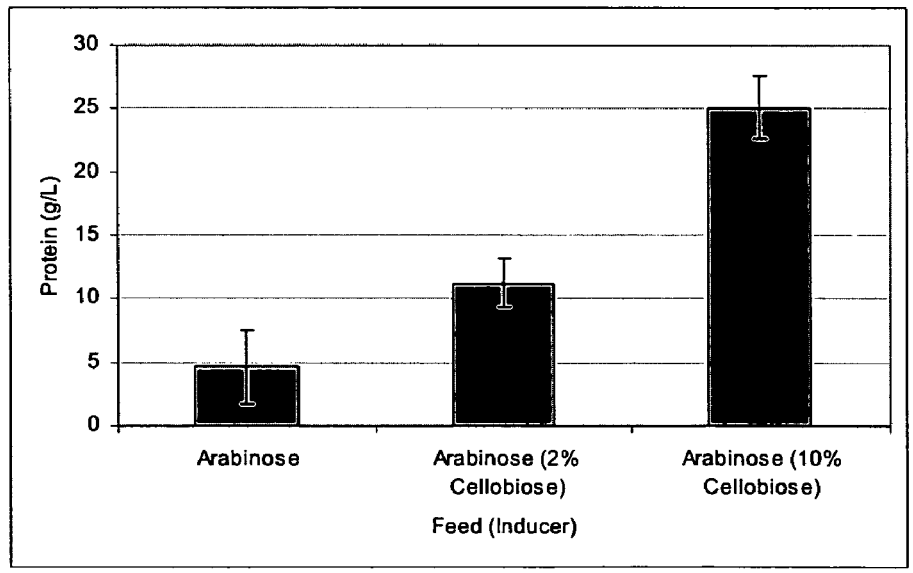
Figure 5:
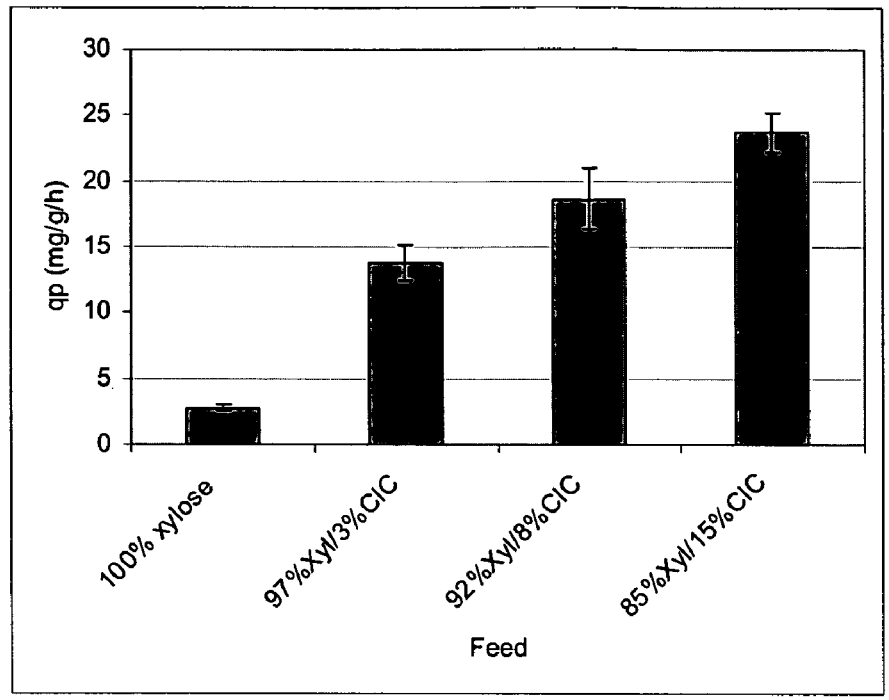
FIG. 5 shows the average specific productivity ($q_p$) in mg secreted protein/g biomass/h of *T. reesei* strain P59G in 14 L fed-batch fermentations in which the carbohydrate fed to the fermentation consisted (A) 0-15% CIC cocktail plus 85-100% xylose as shown or (B) 0-10% cellobiose plus 90-100% arabinose. Each bar shows the average and standard deviation of three independent fermentations.
Figure 5:
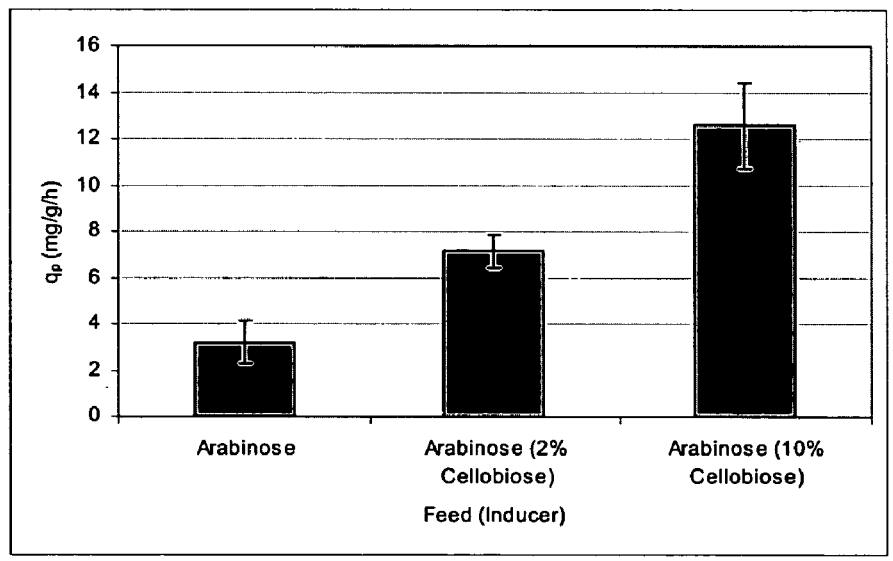

The fed-batch fermentation processes using both HDC and CIC exhibits 4-12 fold higher specific productivity than a corresponding processing using only HDC (Table 6, FIG. 4).

TABLE 6

Specific productivity of 14L fed-batch cultures of *T. reesei* strains used HDC with or without CIC.

| Strain | Carbon Source (HDC/CIC) | $q_p^b$ (mg protein/g cells/h) |
|---|---|---|
| P59G | 100% xylose | 2 |
|  | 97% xylose/3% CIC[a] | 14 |
|  | 92% xylose/8% CIC[a] | 19 |
|  | 85% xylose/15% CIC[a] | 24 |
|  | 100% arabinose | 3.5 |
|  | 90% arabinose/10% cellobiose | 14 |

TABLE 6-continued

Specific productivity of 14L fed-batch cultures of *T. reesei* strains used HDC with or without CIC.

| Strain | Carbon Source (HDC/CIC) | $q_p^b$ (mg protein/g cells/h) |
|---|---|---|
| RutC30 | 100% xylose | 4 |
|  | 92% xylose/8% cellobiose | 23 |

[a]CIC: inducing cocktail comprising, as a function of total carbohydrate, 56% gentiobiose, 14% sophorose, 6% cellobiose, 10% trehalose, 6% maltotriose, 4% glucose and 14% other carbohydrates
[b]For strain P59G, reported values are the average results of three (xylose) or two (arabinose) replicate fermentations; for strain RutC30, the reported values are the results from single fermentations.

Continuous fermentation processes using CIC in combination with HDC mixture produced by the dilute acid-stream pretreatment of a wheat straw (as in U.S. Pat. Nos. 4,461,648 and 5,916,780) or with an equivalent HDC mixture made using pure sugars. These HDC mixtures contained, as a function of total carbohydrate: 81.1% xylose, 11.1% glucose and 7.8% arabinose. As shown in Table 7, the specific productivities of the continuous cultures using HDC mixtures in the form of pretreatment hydrolysate or pure sugars were similar.

TABLE 7

Specific productivity of CSTR cultures of a *T. reesei* strain using CIC and HDC mixtures from pretreatment hydrolysate or pure chemicals.

| Strain | Carbon Source (HDC/CIC) | Average $q_p$ (mg protein/g cells/h)[b] |
|---|---|---|
| P59G | Control: 92% Pure sugars/8% [a]CIC | 27 |
|  | 92% HDC/8% CIC[a] | 24 |

[a]CIC: inducing cocktail comprising, as a function of total carbohydrate, 56% gentiobiose, 14% sophorose, 6% cellobiose, 10% trehalose, 6% maltotriose, 4% glucose and 14% other carbohydrates
[b]Reported values represent the average of two continuous fermentations run using each HDC/CIC mixtures Example 4

Characterization of Cellulase Mixtures Produced in Fed-Batch Fermentations

The individual components of cellulase mixtures produced by the fermentation processes described in Example 2 were separated on the basis of size using SDS poly-acrylamide electrophoresis (SDS-PAGE). For this purpose, the stacking gels were 4% acrylamide, 0.125M Tris-HCl, pH 6.8; separating gels were 12% acrylamide, 0.375M Tris-HCl, pH 8.8. The ratio of stock gel monomer solution used for gel preparation was 37.5:1 acrylamide:bis-acrylamide. Prior to loading, protein samples were denatured by boiling for 5 minutes in buffer containing beta-mercaptoethanol. 10×8×0.075 cm gels were loaded with approximately 10 μg of protein/lane. Electrophoretic separation was done at 200V for approximately 45 minutes. Fractionated proteins were visualized by staining with a Coomassie Brilliant Blue G-250 dye solution.

The proportions of cellulases and hemicellulases fractionated by SDS-PAGE were characterized using scanning gel densitometry. This process entailed first capturing a digital image of a gel stained with Coomassie Brilliant Blue G-250 dye. This was done using a CHEMIGENIUS[2] Bioimaging system (Synoptics Ltd.) and the software package GeneSnap v6.03 (Synoptics Ltd.). The fractionated cellulase and hemicelluase proteins, visualized as distinct bands, were then characterized based on their image signal intensity relative to the sum total of the signal for all bands in a given sample. Signal intensity was determined using the GeneTools v 3.05 software package (Synoptics Ltd.) with default settings enabled. Data was exported to an Excel spreadsheet (Microsoft Inc.) for further analysis.

The specific activity of the cellulases mixtures produced by *T. reesei* fermentations using mixtures of HDC and CIC was determined by measuring the release of reducing sugars from a pretreated wheat straw substrate or from filter paper.

Hydrolysis of filter paper was conducted according to the standard IUPAC methods for the measurement of cellulase activity (Ghose, T. K., 1987, Pure & Appl. Chem. 59: 257-268). Values reported are specific cellulase activities in IU/mg protein.

Hydrolysis of wheat straw was conducted as follows: dilutions of the fermentation filtrates in 50 mM pH 5.0 citrate buffer containing 0.5% sodium benzoate, were complemented with a β-glucosidase preparation from *Aspergillis niger* and incubated with acid pretreated wheat straw prepared as per U.S. Pat. No. 4,461,648; the reaction mixtures were shake at 50° C. for 24 hr and the target cellulose conversion level was greater than 70%. The enzyme activity was calculated by determining the amount of enzyme required to reach the target cellulose conversion level. These activities were normalized to the activity of a control fermentation filtrate produced in a 14 L fed-batch culture of the same strain grown using a carbon source produced by the acid condensation of glucose. The total protein mass tested in the assays for all fermentation filtrates was the same.

As shown in Table 8, the fermentation filtrates produced by *T. reesei* cultures grown with at least 3% CIC in combination with HDC produced higher quality cellulases than the cultures grown with HDC alone. Inclusion of at least 3% CIC in the carbon source fed to the fermentation improved the ratio of cellulase:hemicellulase and the specific activity of the cellulase for hydrolysis of cellulosic substrates.

The embodiments of the invention in which an exclusive property or privilege is claimed are defined as follows:

1. A fermentation process for the production of a cellulase mixture comprising providing a cellulase-secreting host cell of the genus *Trichoderma* or *Hypocrea* with a carbon source for cellulase enzyme production, the carbon source comprising a hemicellulose-derived carbohydrate from 40 weight percent to about 97 weight percent of the total carbon present in the carbon source, and a cellulase-inducing carbohydrate from about 3 weight percent to about 20 weight percent of the total carbon present in the carbon source, for from about 3 to about 30 days, at a temperature of about 20° C. to about 35° C., at a pH of from about 3.0 to about 6.5, and obtaining the cellulose mixture.

2. The fermentation process of claim 1, wherein from 80 weight percent to about 97 weight percent of the total carbon present in the carbon source is the hemicellulose-derived carbohydrate, and wherein from about 8 weight percent to about 15 weight percent of the total carbon present in the carbon source is the cellulase-inducing carbohydrate.

3. The fermentation process of claim 1, wherein the cellulase mixture comprises cellulases and hemicellulases in a ratio of at least 2:1.

4. The fermentation process of claim 1, wherein the cellulase mixture comprises cellulases and hemicellulases in a ratio of at least 3:1.

5. The fermentation process of claim 1, wherein the carbon source comprises one or more additional carbon sources.

6. The fermentation process of claim 5, wherein the one or more additional carbon source is glycerol or an organic acid.

7. The fermentation process of claim 1, wherein the host cell is a strain of *Trichoderma reesei*.

8. The fermentation process of claim 1, wherein the process produces at least 2-fold more secreted cellulase when compared to the amount of secreted cellulose produced in a process in which the carbon source consists of hemicellulose-derived carbohydrates.

9. The fermentation process of claim 1, wherein the process is characterized by having at least a 3-fold increase in specific productivity ($q_p$ measured in mg secreted protein per gram

TABLE 8

Composition of secreted enzyme from *T. reesei* cultures grown in submerged liquid cultures on HDC and CIC in 14L fed-batch fermentation.

| | | | | Relative Cellulase Activity | |
|---|---|---|---|---|---|
| Strain | HDC (%) | % CIC | Cellulase:Hemicellulase ratio | Pretreated lignocellulose[c] | Filter paper[c] |
| P59G** | Glucose control (85) | 15 | 20:1 | 1.0 | n.d. |
| | Xylose (100) | 0 | ~1:1 | n.d. | 0.11 |
| | Xylose (92) | 8[a] | 2:1 | 0.58 | 0.41 |
| | Xylose (85) | 15[a] | 3:1 | 0.62 | n.d. |
| | HDC blend[d] (92) | 8[b] | n.d | n.d. | 0.42 |
| | HDC blend[e] (92) | 8[b] | n.d. | n.d. | 0.52 |
| | Arabinose (100) | 0[b] | 0.8:1 | n.d. | 0.05 |
| | Arabinose (98) | 2[b] | 1.5:1 | 0.31 | n.d. |
| | Arabinose (90) | 10[b] | 2.4:1 | 0.84 | 0.66 |
| RutC30 | Xylose (100) | 0[b] | 2:1 | n.d. | <0.05 |
| | Xylose (92) | 8[b] | 3:1 | n.d | 0.38 |

[a]CIC for these fermentations was inducing cocktail comprising, as a function of total carbohydrate, 56% gentiobiose, 14% sophorose, 6% cellobiose, 10% trehalose, 6% maltotriose, 4% glucose and 14% other carbohydrates
[b]CIC for these fermentations was cellobiose.
[c]Relative hydrolysis activity on a pretreated lignocellulosic substrate or filter paper. Values represent the average of triplicate assays run on the secreted enzymes from filtrates of three (HDC = xylose) or two (HDC = arabinose) independent 14L fermentations (n.d. = not determined).
[d]Mixture of pure sugars (81.1% xylose, 11.1% glucose and 7.8% arabinose).
[e]Mixture of sugars in pretreatment hydrolysate (81.1% xylose, 11.1% glucose, 7.8% arabinose)

fungal biomass per hour) when compared to $q_p$ in a process in which the carbon source consists of hemicellulose-derived carbohydrates.

10. The fermentation process of claim 1, wherein the process is characterized by having at least a 5-fold increase in specific productivity ($q_p$ measured in mg secreted protein per gram fungal biomass per hour) when compared to $q_p$ in a process in which the carbon source consists of hemicellulose-derived carbohydrates.

11. The fermentation process of claim 1, wherein the process is fed-batch.

12. The fermentation process of claim 1, wherein the process is continuous.

13. The fermentation process of claim 1, wherein the process is conducted aerobically.

14. A method for hydrolyzing a cellulosic substrate, comprising the steps of obtaining the cellulase mixture according to claim 1 and contacting said cellulase mixture with a cellulosic substrate.

15. A method for hydrolyzing a cellulosic substrate according to claim 14, wherein said cellulosic substrate is a pretreated lignocellulosic substrate.

16. A method of hydrolyzing a cellulosic substrate comprising
adding the cellulase mixture produced by the fermentation process of claim 1 to the cellulosic substrate to produce a reaction mixture, wherein the concentration of cellulose in the reaction mixture is from about 1 g/L to about 200 g/L and the cellulase mixtures is added at a concentration from about 0.1 mg protein/ g cellulose to about 100 mg protein/g cellulose;
incubating the reaction mixture for a period of time from about 4 to about 120 hours, at a temperature from about 30° to about 60° C., and at a pH from about 3.5 to about 7.0 to hydrolyze the cellulosic substrate and produce reaction products.

17. The method of claim 16, wherein the reaction products include hemicellulase-derived carbohydrate, glucose, oligosaccarides, cellulase-inducing carbohydrates, and a combination thereof.

18. The method of claim 16, wherein the cellulosic substrate is a pretreated lignocellulosic substrate.

* * * * *

UNITED STATES PATENT AND TRADEMARK OFFICE
CERTIFICATE OF CORRECTION

| | | |
|---|---|---|
| PATENT NO. | : 8,093,019 B2 | Page 1 of 3 |
| APPLICATION NO. | : 12/200492 | |
| DATED | : January 10, 2012 | |
| INVENTOR(S) | : Jason B. Edwards et al. | |

It is certified that error appears in the above-identified patent and that said Letters Patent is hereby corrected as shown below:

ON TITLE PAGE [56] REFERENCES CITED:

Other Publications, Under Margolles-Clark, "*hemicellulose*" should read --hemicellulose--.

ON TITLE PAGE [56] REFERENCES CITED:

Other Publications, Under Sternberg, "Tricoderma" should read --Trichoderma--.

ON TITLE PAGE [56] REFERENCES CITED:

Other Publications, Under Fenner, "Elluted" should read --Eluted--.

COLUMN 1:

Line 20, "Cellulose," should read --Cellulose--;
    Line 23, "in via" should read --via--; and
    Line 29, "variety" should read --a variety--.

COLUMN 2:

Line 27, "saw-dust" should read --sawdust--; and "hydroysates" should read --hydrolysates--;
    Line 33, "saw dust" should read --sawdust--; and "25-40%" should read --25-37%--;
    Line 34, "5-9%" should read --0.5-9.4%--;
    Line 39, "cellulose" should read --cellulase--;
    Line 47, "(Maccabe," should read --(MacCabe,--; and
    Line 58, "technol. 681:21-40;" should read --technol. 68:21-40;--.

Signed and Sealed this
Seventeenth Day of April, 2012

David J. Kappos
*Director of the United States Patent and Trademark Office*

CERTIFICATE OF CORRECTION (continued)
U.S. Pat. No. 8,093,019 B2

COLUMN 3:

Line 10, "40% the" should read --40% of the--.

COLUMN 4:

Line 55, "consisted" should read --consisted of--.

COLUMN 5:

Line 38, "carried" should read --carried out--.

COLUMN 6:

Table 1, "carbohydrates" should read --carbohydrates.--.

COLUMN 8:

Line 6, "maybe" should read --may be--;
    Line 12, "cont." should read --content.--;
    Line 26, "gen" should read --gene--; and
    Line 48, "preferable," should read --preferably,--.

COLUMN 9:

Table 2, "carbohydrates" should read --carbohydrates.--; and
    Table 3, "carbohydrates" should read --carbohydrates.--.

COLUMN 10:

Line 3, "substrate," should read --substrate--;
    Line 6, "there" should read --ther--;
    Line 7, "between" should read --ebetween--;
    Line 19, "from of" should read --from a--;
    Line 20, "or of" should read --or--; and
    Line 23, "oligosaccarides" should read --oligosaccharides--.

COLUMN 11:

Line 5, "Trichoderma" should read --*Trichoderma*--.

COLUMN 12:

Line 43, "*inoculum*" should read --inoculum--.

COLUMN 13:

Line 24, "carbohydrates" should read --carbohydrates.--; and
    Table 5, "fermentations;." should read --fermentations.--.

COLUMN 14:

Table 6, "carbohydrates" should read --carbohydrates.--;
    Table 7, "carbohydrates" should read --carbohydrates.--; and "mixtures" should read --mixtures.--; and
    Line 55, "beta" should read --*beta*--.